United States Patent
Koster et al.

(10) Patent No.: US 8,480,807 B2
(45) Date of Patent: Jul. 9, 2013

(54) METHOD AND AN APPARATUS FOR CLEANING AND/OR STERILIZATION OF AN OBJECT PROVIDED IN A SEALED ENCLOSURE

(75) Inventors: Norbertus Benedictus Koster, Delft (NL); René Koops, The Hague (NL); Kemal Agovic, The Hague (NL); Fokko Pieter Wieringa, Elst (NL)

(73) Assignee: Nederlandse Organisatie voor toegepast-natuurwetenschappelijk onderzoek TNO (NL)

( * ) Notice: Subject to any disclaimer, the term of this patent is extended or adjusted under 35 U.S.C. 154(b) by 44 days.

(21) Appl. No.: 13/124,261

(22) PCT Filed: Oct. 16, 2009

(86) PCT No.: PCT/NL2009/050626
§ 371 (c)(1),
(2), (4) Date: Jun. 27, 2011

(87) PCT Pub. No.: WO2010/044669
PCT Pub. Date: Apr. 22, 2010

(65) Prior Publication Data
US 2011/0247649 A1    Oct. 13, 2011

(30) Foreign Application Priority Data
Oct. 17, 2008 (EP) ...................... 08166967

(51) Int. Cl.
*C25F 1/00* (2006.01)
(52) U.S. Cl.
USPC .............. 134/1.1; 134/21; 134/26; 134/30; 134/36; 134/42; 216/59; 216/60; 216/67; 216/68; 216/69; 216/70; 216/71

(58) Field of Classification Search
USPC ......... 216/59, 60, 67, 68, 69, 70, 71; 134/1.1, 134/21, 26, 30, 36, 42
See application file for complete search history.

(56) References Cited

U.S. PATENT DOCUMENTS

| 3,851,436 A | 12/1974 | Fraser et al. |
| 4,321,232 A * | 3/1982 | Bithell ............................ 422/23 |

(Continued)

FOREIGN PATENT DOCUMENTS

| EP | 1726314 A1 | 11/2006 |
| EP | 1916523 A1 | 4/2008 |

OTHER PUBLICATIONS

Lerouge et al., "Plasma Sterilization: A Review of Parameters, Mechanisms, and Limitations", Plasmas and Polymers, vol. 6, No. 3, pp. 175-188, Sep. 2001, Plenum Publishing Corporation.

(Continued)

*Primary Examiner* — Bibi Carrillo
(74) *Attorney, Agent, or Firm* — Waddey & Patterson, P.C.; Rebecca M. Barnett; James R. Cartiglia

(57) ABSTRACT

The invention relates to a method of cleaning and/or sterilization of an object provided in a hermetically sealed enclosure, providing a pressure difference between an internal volume of the enclosure and surroundings and generating a plasma solely inside the enclosure for said cleaning and/or sterilization of the object. The invention further relates to an apparatus for enabling the same. The apparatus 10 comprises a vacuum chamber 1, which can be evacuated using a vacuum pump 2, and a source 3 arranged to generate plasma of a suitable gas in an enclosure 8, which is substantially hermetically closed with respect to the atmosphere of the vacuum chamber. The enclosure 8 may be of a flexible type or may be manufactured from a rigid material. In case when the enclosure is rigid the pressure inside the enclosure may be lower than an outside pressure.

13 Claims, 2 Drawing Sheets

U.S. PATENT DOCUMENTS

| | | | |
|---|---|---|---|
| 5,897,831 A * | 4/1999 | Jacob et al. | 422/22 |
| 6,007,770 A * | 12/1999 | Peiper et al. | 422/22 |
| 6,261,518 B1 * | 7/2001 | Caputo et al. | 422/22 |
| 6,558,621 B1 * | 5/2003 | Banks et al. | 422/28 |
| 6,875,400 B2 * | 4/2005 | Speer et al. | 422/22 |
| 2002/0136679 A1 * | 9/2002 | Frieze et al. | 422/300 |
| 2004/0040833 A1 * | 3/2004 | Schaepkens et al. | 204/164 |
| 2005/0205206 A1 | 9/2005 | Lembersky | |
| 2010/0178198 A1 * | 7/2010 | Moisan et al. | 422/23 |
| 2012/0183437 A1 * | 7/2012 | Keener et al. | 422/23 |

OTHER PUBLICATIONS

PCT/NL2009/050626 International Search Report, mailing date Dec. 30, 2009.

* cited by examiner

METHOD AND AN APPARATUS FOR CLEANING AND/OR STERILIZATION OF AN OBJECT PROVIDED IN A SEALED ENCLOSURE

FIELD OF THE INVENTION

The invention relates to a method of cleaning and/or sterilization of an object provided in a sealed enclosure. The invention further relates to an apparatus for enabling the same.

BACKGROUND OF THE INVENTION

An embodiment of the method as is set forth in the foregoing is known from WO81/02809. According to the known method a porous flexible package is placed in plasma and an object contained in the porous package is sterilized through the package. The sterilization process is initiated by ions and radicals which have entered the inner space of the enclosure by diffusion from the outside of the enclosure. The porous package is therefore manufactured from a permeable material for neutralizing plasma ions while allowing suitable reactive components to diffuse inside the package for sterilizing the object.

It is a disadvantage of the known method that efficiency of the sterilization process may be substantially reduced by the porous material of the package intercepting the ion flux. It is a further disadvantage of the known method that energy may be spilled as plasma is generated in a remote area (i.e. outside the enclosure) whereas only a small part of plasma particles is used for sterilization.

Another embodiment of the method as is set forth in the opening paragraph is known from U.S. Pat. No. 6,007,770. In the known method an object conceived to be sterilized in being provided in a rigid enclosure, which is positioned between two electrode plates for generating plasma inside the enclosure, the enclosure functioning as a dielectric medium for inducing a barrier discharge.

It is a disadvantage of the method known from U.S. Pat. No. 6,007,770 that the enclosure is to be positioned in a contact with the electrode plates, which may cause damages on the enclosure surface thereby possibly corrupting the sterilization process.

SUMMARY OF THE INVENTION

It is an object of the invention to provide a method of cleaning and/or sterilization of an object provided in a sealed enclosure, said method having increased reliability and, optionally, an increased detectability of possible sterilization faults.

To this end the method according to the invention comprises the steps of:
providing the enclosure in an area of plasma generation of a plasma generator;
providing a pressure difference between an internal volume of the enclosure and environment of the plasma generator;
generating plasma solely inside the enclosure using the plasma generator for said cleaning and/or sterilization.

It will be appreciated that the invention is suitable for cleaning and/or sterilization of an object in either a flexible enclosure, or in a rigid enclosure. Examples of a flexible enclosure comprise, but are not limited to, a plastic bag, or a wrap of a different suitable material, like a foil conceived at least partially to be shaped or wrapped about the object for enclosing it. Preferably, the flexible enclosure is weldable. More preferably, the flexible enclosure is evacuated before the cleaning an/or sterilization process have commenced. Examples of a rigid enclosure comprise, but are not limited to, a box, a vessel, or the like, capable of substantially hermetically enclosing an object in its inner volume.

In accordance with the invention due to the pressure difference between the inner volume of the enclosure and the outer atmosphere, i.e. the atmosphere of the plasma area of a plasma generator, the plasma is generated substantially solely inside the enclosure. This has an advantage that plasma is generated substantially only inside the enclosure and substantially no particle loss occurs on a surface of the enclosure as ions and electrons and radicals of the plasma do not have to traverse the material of the enclosure for reaching the object. Accordingly, all energy used for plasma generation is purposefully used.

It will be appreciated that if the enclosure is rigid, the pressure outside the enclosure may be atmospheric and the pressure inside the enclosure may be decreased. As a result, it is possible to ignite the plasma inside the rigid enclosure, for example using microwaves, whereas substantially no plasma will be ignited outside the enclosure.

It will be further appreciated that in case a flexible enclosure is used, the pressure difference between the inner volume of the enclosure and an outer atmosphere is preferably set to a positive value, so that the pressure in the inner volume is higher than the pressure in the outer volume. However, at the same time the pressure inside the enclosure may-be sub-atmospheric. For example, suitably packed medical instruments may be cleaned and/or sterilized according to the method of the invention.

It will be still further appreciated that the method according to the invention provides a further advantage, that is, a possibility of re-sterilizing a packed object which has been stored in a hermetically sealed enclosure during a prolonged amount of time. In this case the object may be re-sterilized according to the method of the invention without opening the enclosure.

In this case, an embodiment of the method according the invention further comprises the steps of:
placing the object provided in the hermetically closed enclosure in a vacuum chamber of the plasma generator;
evacuating the vacuum chamber to a lower pressure with respect to a pressure inside the enclosure.

Due to the fact that the flexible enclosure is substantially hermetically closed with respect to the outer atmosphere, the volume of the enclosure may increase when the vacuum chamber is evacuated. Such deformation of the flexible enclosure may be seen as an indicator that the enclosure was indeed hermetically closed and remains hermetically closed after cleaning and/or sterilization using plasma.

Accordingly, when the chamber is aired, the flexible enclosure will resume its original state, for example closely enveloping or otherwise contacting the object. When the flexible enclosure does not change its shape upon evacuation of the vacuum chamber or does not return to its original condition post cleaning/sterilization, a decision may be drawn that the object is not sterile, pursuant to a possible damage of the enclosure. It will be appreciated that such decision may be taken by a person or in an automatic way. For example, an image of the enclosure may be picked-up before the evacuation of the vacuum chamber and post evacuation. Should these images show no difference, a decision may be taken than the enclosure is corrupted.

It will be appreciated that many embodiments of enabling an automatic control whether the enclosure is still hermetic are contemplated. For example, the plasma generator may be provided with a switch which is conceived to be suitably displaced by the envelope when it expands. The switch may be used as a control signal for suitable analysis.

In a further embodiment the method according to the invention comprises the step of confining the enclosure for controlling the pressure inside the enclosure.

When a pre-evacuated hermetically closed enclosure is positioned in a vacuum chamber and a positive pressure difference between the inner volume of the enclosure and the atmosphere of the vacuum chamber is preserved the enclosure will tend to expand due to its flexibility and the positive pressure difference. Preferably, such enclosure is reasonably confined for controlling its expanded volume and for controlling internal pressure of the enclosure. This has an advantage that efficiency of plasma generation within the enclosure is increased, as there is a match between a necessary gas pressure inside the enclosure and operational parameters of the plasma source. It will be appreciated that the switch as discussed above may be positioned on such confinement member.

Preferably, plasma inside the enclosure is generated by a device remotely arranged with respect to a surface of the enclosure. This has an advantage that no mechanical contact between the enclosure and a plasma generating source is required minimizing a risk of mechanical damage of the enclosure. Preferably, the device comprises a radio-frequency source or a microwave source.

In a still further embodiment of the method according to the invention, a parameter of the plasma during cleaning and/or sterilization is monitored.

For this purpose the enclosure may comprise a suitable indicator, positioned next to the object conceived to be cleaned and/or sterilized. Examples of a suitable indicator comprise a sample with a coating which is arranged to change a physical property, like color, when plasma has removed the coating. Another example of a suitable indicator is a sample with a carbon coating which is arranged to change transmittance according to a plasma dose received, or the like. It will be appreciated that a suitable plurality of possible implementations of the indicator are possible, some of which are known from US 2007/0143032.

An apparatus, according to the invention, for cleaning and/or sterilization of an object provided in a hermetically closed enclosure, comprises:
  an evacuation unit for evacuating atmosphere of the enclosure to a working pressure;
  a vacuum chamber for receiving the enclosure and for providing a pressure difference between the working pressure and a pressure inside the vacuum chamber;
  a plasma source for generating plasma solely inside the enclosure.

In an embodiment of the apparatus as is set forth in the foregoing, the apparatus is further provided with a packing unit comprising a material of the enclosure for arranging the object inside the enclosure.

It is found to be advantageous to integrate a packing process, for example using a flexible enclosure with a sterilization unit in one apparatus. Advantageously, such apparatus comprises a packing unit arranged to enclose an object conceived to be cleaned. Preferably, the packing unit is arranged to vacuum pack the object in the enclosure and to substantially hermetically close the enclosure with respect to ambient surroundings. Preferably, an internal pressure of the enclosure is set to a value in a range of about 0.1-10 mbar. When a material of the enclosure is weldable, the apparatus preferably comprises a heater arranged to seal the enclosure by application of local heat. For example, a heated wire, or a heated bar may be used for that purpose.

In a further embodiment of the apparatus according to the invention, it further comprises a gas source for flushing an atmosphere of the enclosure.

It is found to be advantageous to flush the atmosphere of the enclosure for removing undesired microscopic trace materials on the surface of the object, like dust and/or for filling the enclosure with a desired gas for plasma generation.

In a still further embodiment of the apparatus according to the invention, the plasma source comprises a radio frequency source or a microwave source.

These and other aspects of the invention will be described in more detail with reference to drawings, wherein like reference numerals indicate like elements. It will be appreciated that the drawings are presented for illustrative purposes only and may not be used for limiting the scope of the appended claims.

DETAILED DESCRIPTION OF THE DRAWINGS

Figure 1:
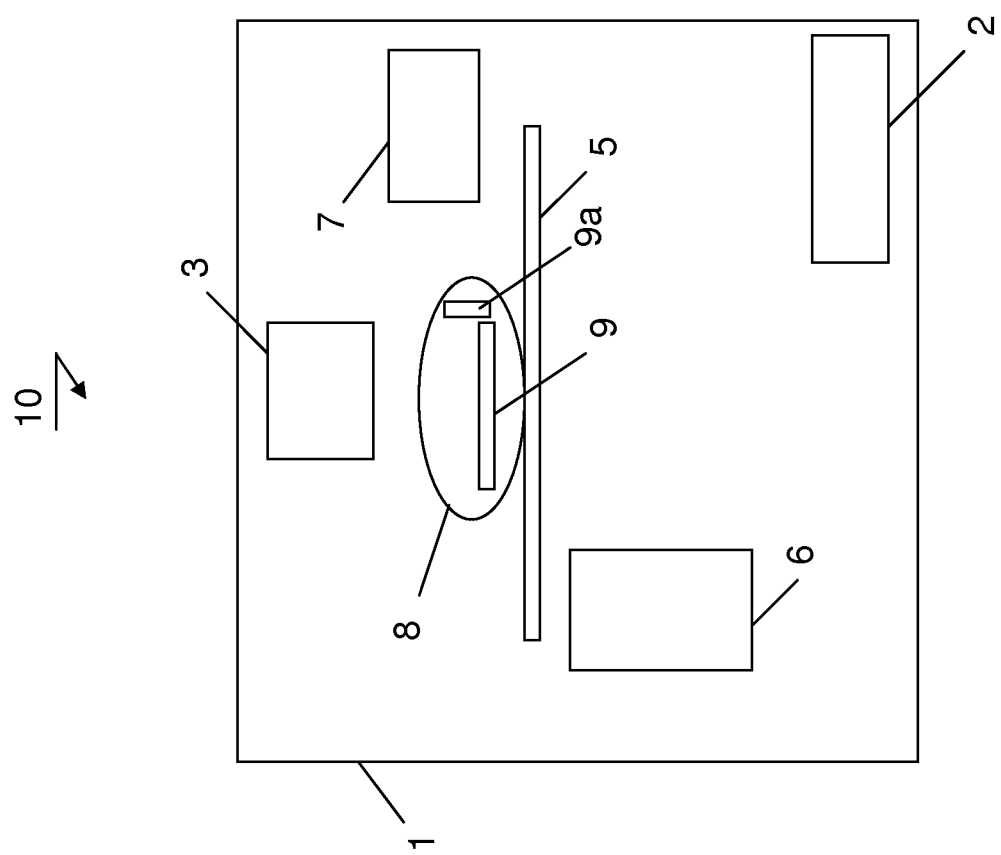
FIG. 1 presents schematically an embodiment of an apparatus according to the invention.

FIG. 1 presents schematically an embodiment of an apparatus according to the invention. The apparatus 10 comprises a vacuum chamber 1, which can be suitably evacuated using a vacuum pump 2. Preferably, a pressure inside the vacuum chamber 1 is set to a value of about 0.1-10 mbar. The apparatus 10 further comprises a source 3 arranged to generate plasma of a suitable gas, for example, air, argon, helium, hydrogen, oxygen or a mixture thereof, in an enclosure 8, which is substantially hermetically closed with respect to the atmosphere of the vacuum chamber. The enclosure 8 may be positioned on a suitable support 5. The enclosure 8 may be of a flexible type or may be manufactures from a rigid material. Preferably, when for a material of the enclosure 8 a flexible, preferably weldable, material is selected, the apparatus 10 preferably comprises a packing unit 6 for enclosing the object 9 conceived to be cleaned and/or sterilized. For closing the enclosure, the packing unit may comprise a heater (not shown), for example a heated wire or a heated bar for thermally sealing the enclosure. Preferably, the packing unit 6 is arranged to "vacuum"-pack the object, so that pressure inside the enclosure is about 0.1-10 mbar.

It will be appreciated that prior to sealing or to closing the enclosure 8, its inner atmosphere, preferably, together with the object 9 may be flushed using a suitable gas, for example, air, argon, helium, hydrogen, oxygen or a mixture thereof, which may be provided from a gas source 7. Preferably, this gas is used as a source of plasma inside the enclosure 8.

For generating plasma inside the enclosure, the apparatus comprises a plasma source, for example an RF source or a microwave source. When a microwave source is used, the plasma generated inside the enclosure may be localized in an area around a small maximum of the microwave field, which may be preferable for cleaning and/or sterilizing of small objects, like wafers. It will be appreciated that the term "object" relates to any suitable item which may be cleaned using plasma. Examples of the object comprise medical equipment, like syringes, needles, catheters and electronic devices, like wafers and so on.

In accordance with an aspect of the invention the enclosure may be provided with an indicator 9a for on-line monitoring of plasma parameters. For example the indicator 9a may comprise an item which may change a physical property, like a color a transmittance, or a shape in response to a received plasma dose. Use of such indicator is advantageous as it may indicate the sterile condition of the object even if it is being stored on a shelf post cleaning/sterilization.

It will be appreciated that a flexible enclosure may be hermetically sealed having an inner pressure in the range of 0.1 mbar-10 mbar. Due to the flexibility of the enclosure the volume is kept small when the outside pressure is higher than the internal pressure. To generate plasma inside the enclosure it is necessary to place the enclosure in a chamber which can achieve much lower pressured than needed for a plasma, i.e, pressures less than 0.01 mbar. Due to the fact that the pressure inside the bag satisfies plasma generation conditions, the plasma will be generated solely inside the enclosure. When an MW or RF field is applied the plasma will ignite inside the enclosure and the cleaning/sterilization process may commence. Therefore, the composition of the gas outside the enclosure is not relevant, as plasma will be generated solely inside the enclosure.

In case a rigid enclosure is used in the method according to the invention the following applies. Also in this case pressure inside the rigid enclosure is provided which satisfies plasma generation conditions, i.e. the pressure is between 0.1 and 10 mbar. It is possible to generate plasma in two ways: use a vacuum chamber as described above and apply a MW or RF field to ignite the plasma. Alternatively, the rigid enclosure may be placed in a chamber with an atmospheric pressure and an MW or RF field may be applied, like in the ordinary microwave oven. Also in this case no plasma is formed outside the enclosure because the pressure is too high to generate plasma using this excitation method.

It will be appreciated that in both cases (flexible or rigid enclosure) evacuation of the enclosure may be done by a combined evacuation and sealing device. In the case of the rigid enclosure the enclosure can also be fitted with a vacuum valve, connected to a vacuum pump and be evacuated, when the desired pressure is reached the valves may be closed and the pump may be disconnected. The evacuation and sealing device for the flexible enclosure are commercially available including a flush unit for supplying flush gas.

Thus, according to the method of the invention sterilization and cleaning process is simplified whereas contamination risks due to repacking are substantially reduced. In addition, due to the fact that plasma is generated solely inside the volume accommodating the object, energy used for plasma generation is saved as plasma particles are generated in a direct vicinity of the object and do not have to diffuse via any packing material.

Figure 2:
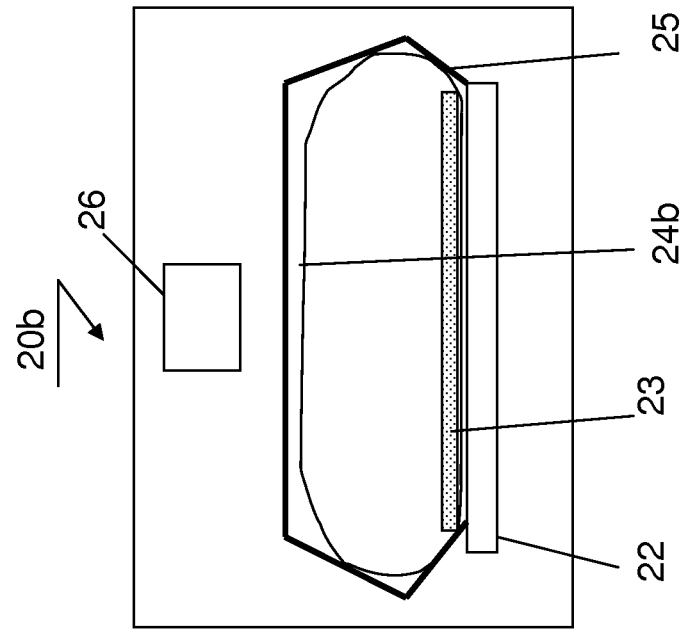
FIG. 2 presents illustrates schematically a process of plasma cleaning in an evacuated enclosure.
Figure 2:
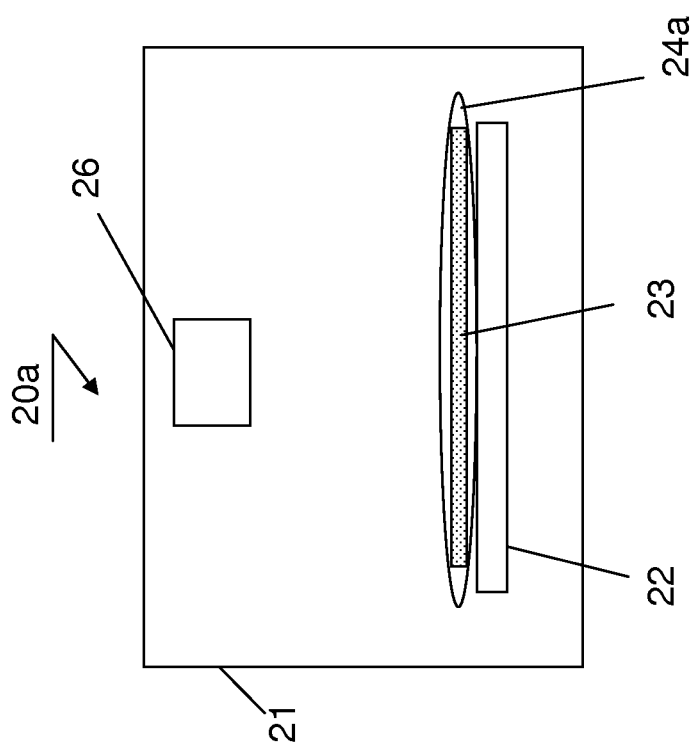

FIG. 2 presents illustrates schematically a process of plasma cleaning in an evacuated enclosure. In accordance with the method of the invention an object 23 conceived to be sterilized, being enclosed in a suitable substantially hermetically closed enclosure, is provided inside a vacuum chamber of a cleaning apparatus. It will be appreciated that the object 23 may be pre-packed, or it may be packed or positioned inside the enclosure in the cleaning apparatus, as is set forth in the foregoing, which may rest on a support table 22. Preferably a pressure inside the enclosure is set to a value of about 0.1-10 mbar. View 20a schematically indicates an initial condition, when the pressure inside the vacuum chamber 21 may be higher than the pressure inside the enclosure 24a. In this condition the enclosure is substantially flat, which indicates that it's atmosphere is closed with respect to the atmosphere of the vacuum chamber 21. In accordance with the invention, the pressure inside the vacuum chamber may be set to a lower value, for example to 0.01 mbar, than the internal pressure of the enclosure 24a. As a result (see view 20b), the enclosure 24b may expand, which may be used as an indicator than the enclosure is still substantially hermetically closed. The volume of the enclosure may be confined by box 25 for controlling a maximum expansion rate of the material of the enclosure. This has an advantage that damage of enclosure due to excessive expansion is prevented and that the pressure inside the enclosure 24b is controlled. Finally, the plasma source 26 may be switched on for generating plasma substantially only inside the enclosure 24b and the object 23 is cleaned and/or is sterilized. It will be appreciated that a level of the pressure in the vacuum chamber is set to such a level that no plasma outside the enclosure is generated.

Table 1 presents indications on the cleaning/sterilization efficiency according to the invention.

TABLE 1

| Gas mixture | P_bag mbar | T_exposure minutes | Peak MW power Watts | Duty cycle % | Carbon removal nm |
|---|---|---|---|---|---|
| He | ~7 | 30 | 100 | 10 | 0.4 |
| He | ~5 | 60 | 100 | 10 | 1.0 |
| He | ~4 | 90 | 100 | 10 | 0.8 |
| He | ~5 | 120 | 100 | 10 | 1.2 |
| He/O2 # | ~9 | ~3 | 800 | 10 | ~20 |
| He/O2 | ~8 | 20 | 800 | 10 | 4.7 |

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

The invention claimed is:

1. A method of cleaning and/or sterilization of an object provided in an hermetically closed enclosure, comprising the steps of:
    providing the enclosure in a chamber comprising an area of plasma generation by a plasma generator;
    providing a pressure difference between an internal volume of the enclosure and the chamber;
    generating plasma solely inside the enclosure for said cleaning and/or sterilization of said object using the plasma generator.

2. A method according to claim 1, wherein pressure inside the enclosure is set to a higher value than the pressure of the chamber.

3. A method according to claim 1, wherein the enclosure is rigid and the pressure inside the enclosure is lower than the pressure outside the enclosure.

4. A method according to claim 1, wherein plasma inside the enclosure is generated by the plasma generator remotely arranged with respect to the enclosure.

5. A method according to claim 1, further comprising a step of monitoring a parameter of the plasma during said cleaning and/or sterilization.

6. A method according to claim 1, wherein the enclosure comprises a removable coating.

7. A method according to claim 1, wherein the enclosure is flexible.

8. A method according to claim 2, wherein the enclosure is flexible.

9. A method according to claim 4, wherein the plasma generator comprises a radio-frequency source or a microwave source.

10. A method according to claim 5, wherein said parameter is monitored using an indicator positioned inside the enclosure.

11. A method according to claim 8, further comprising a step of confining the enclosure for controlling the pressure inside the enclosure.

12. A method according to claim 10, wherein a color of the indicator changes upon interaction with plasma particles.

13. A method according to claim 10, wherein the indicator comprises a carbon coating.

* * * * *

UNITED STATES PATENT AND TRADEMARK OFFICE
CERTIFICATE OF CORRECTION

PATENT NO. : 8,480,807 B2
APPLICATION NO. : 13/124261
DATED : July 9, 2013
INVENTOR(S) : Norbertus Benedictus Koster et al.

It is certified that error appears in the above-identified patent and that said Letters Patent is hereby corrected as shown below:

On the title page item (73), replace "onderziek" with "onderzoek".

Signed and Sealed this
Fifteenth Day of October, 2013

Teresa Stanek Rea
*Deputy Director of the United States Patent and Trademark Office*